United States Patent
Peeters et al.

(10) Patent No.: US 9,765,406 B2
(45) Date of Patent: Sep. 19, 2017

(54) TOOLS AND METHOD FOR THE DETECTION AND QUANTIFICATION OF GENETICALLY DIVERSE HIV-1, SIVCPZ AND SIV GOR VIRUSES

(71) Applicant: INSTITUT DE RECHERCHE POUR LE DEVELOPPEMENT (IRD), Marseilles (FR)

(72) Inventors: Martine Peeters, Montferrier sur lez (FR); Lucie Etienne, Pompertuzat (FR)

(73) Assignee: INSTITUT DE RECHERCHE POUR LE DEVELOPPEMENT (IRD), Marseilles (FR)

( * ) Notice: Subject to any disclaimer, the term of this patent is extended or adjusted under 35 U.S.C. 154(b) by 101 days.

(21) Appl. No.: 14/441,692

(22) PCT Filed: Nov. 8, 2013

(86) PCT No.: PCT/EP2013/073354
§ 371 (c)(1),
(2) Date: May 8, 2015

(87) PCT Pub. No.: WO2014/072457
PCT Pub. Date: May 15, 2014

(65) Prior Publication Data
US 2015/0275316 A1    Oct. 1, 2015

(30) Foreign Application Priority Data
Nov. 9, 2012  (EP) .................................... 12192087

(51) Int. Cl.
| | | |
|---|---|---|
| C12Q 1/68 | (2006.01) | |
| C07H 21/02 | (2006.01) | |
| C07H 21/04 | (2006.01) | |
| C12Q 1/70 | (2006.01) | |

(52) U.S. Cl.
CPC ....... C12Q 1/703 (2013.01); *C12Q 2600/158* (2013.01)

(58) Field of Classification Search
None
See application file for complete search history.

(56) References Cited

U.S. PATENT DOCUMENTS

| | | |
|---|---|---|
| 6,623,920 B1 | 9/2003 | Bee et al. |
| 7,097,979 B2 | 8/2006 | Bee et al. |
| 7,425,417 B2 | 9/2008 | Bee et al. |
| 7,723,040 B2 | 5/2010 | Bee et al. |
| 2004/0053223 A1 | 3/2004 | Bee et al. |
| 2007/0015142 A1 | 1/2007 | Bee et al. |
| 2009/0053692 A1 | 2/2009 | Bee et al. |

FOREIGN PATENT DOCUMENTS

| | | |
|---|---|---|
| WO | 91-08308 | 6/1991 |
| WO | 01-04361 | 1/2001 |

OTHER PUBLICATIONS

Avettand-Fenoel et al. J Med Virology. 2009. 81:217-223.*
Drosten et al Clinical Chemistry. 2006. 52(7): 1258-1266.*
Database Geneseq [Online] Sep. 10, 1991, 3' primer S2 for detecting HIV-1. II XP002688736, retrieved from EBI accession No. GSN:AAQ12362, Database accession No. AAQ12362.
Database Geneseq [Online] Apr. 18, 2001,"HIV-1 detection PCR primer SEQ ID No. 23." XP002688738, retrieved from EBI accession No. GSN:AAF56555 Database accession No. AAF56555 sequence.
Database EMBL [Online] Feb. 6, 2001,"Sequence 23 from Patent W00104361.", XP002688739, retrieved from EBI accession No. EM PAT:AX074110 Database accession No. AX074110 sequence.
Database EMBL [Online] Oct. 9, 2006, "Sequence 9 from U.S. Pat. No. 7,097,979.", XP002688832, retrieved from EBI accession No. EM PAT:AR929452 Database accession No. AR929452.
Etienne Lucie et al: "Noninvasive follow-up of simian immunodeficiency virus infection in wild-living nonhabituated western lowland gorillas in Cameroon", Journal of Virology, American Society for Microbiology, US, vol. 86, No. 18, Sep. 1, 2012 , pp. 9760-9772.
International Search report, dated Dec. 18, 2013; Application No. PCT/EP2013/073354.
Written Opinion of the International Searching Authority, dated Dec. 18, 2013; Application No. PCT/EP2013/073354.

* cited by examiner

*Primary Examiner* — Carla Myers
(74) *Attorney, Agent, or Firm* — Young & Thompson

(57) ABSTRACT

The oligonucleotide of sequence SEQ ID No.1:
5'-CTAGAGATCCCTCAGA-3',
and the complementary sequence thereof of sequence SEQ ID No.2:
5'-TCTGAGGGATCTCTAG-3'
useful as probes to detect and quantify all HIV-1 circulating forms and their precursors SIVcpz/SIVgor.

2 Claims, 3 Drawing Sheets

A

B

Figure 1:
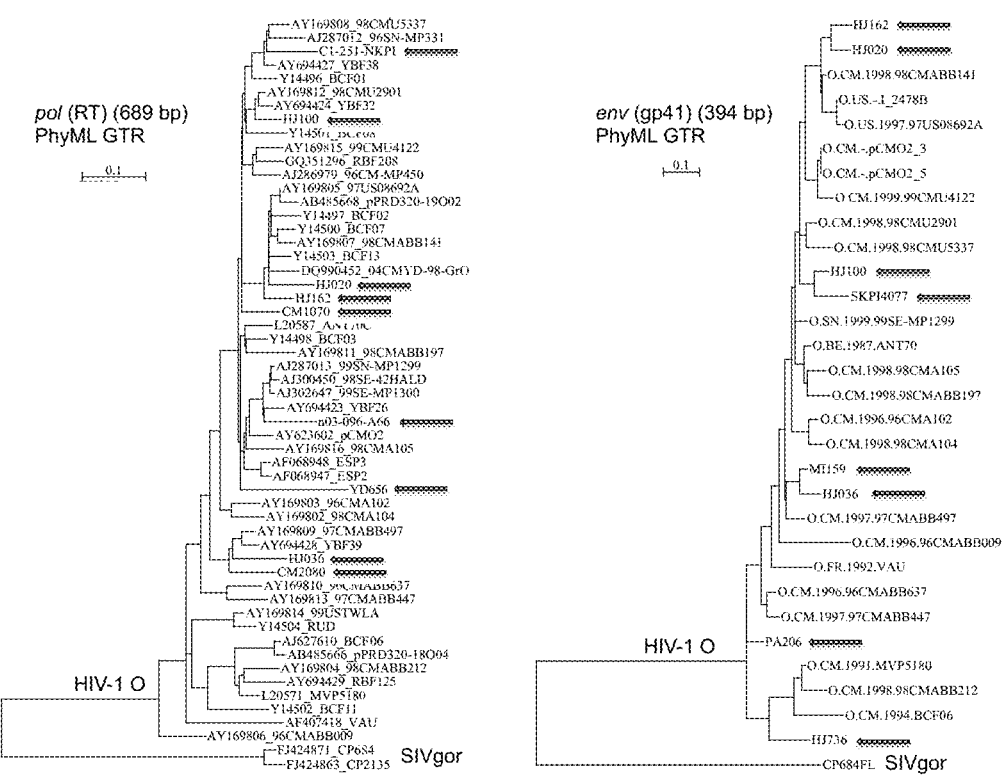

SEQUENCE LISTING

```
<160> NUMBER OF SEQ ID NOS: 5

<210> SEQ ID NO 1
<211> LENGTH: 16
<212> TYPE: DNA
<213> ORGANISM: Artificial Sequence
<220> FEATURE:
<223> OTHER INFORMATION: Nucleic fragment

<400> SEQUENCE: 1
ctagagatcc ctcaga                                                16

<210> SEQ ID NO 2
<211> LENGTH: 16
<212> TYPE: DNA
<213> ORGANISM: Artificial Sequence
<220> FEATURE:
<223> OTHER INFORMATION: Nucleic fragment

<400> SEQUENCE: 2
tctgagggat ctctag                                                16

<210> SEQ ID NO 3
<211> LENGTH: 18
<212> TYPE: DNA
<213> ORGANISM: Artificial Sequence
<220> FEATURE:
<223> OTHER INFORMATION: Amorce primer

<400> SEQUENCE: 3
ssctcaataa agcttgcc                                              18

<210> SEQ ID NO 4
<211> LENGTH: 21
<212> TYPE: DNA
<213> ORGANISM: Artificial Sequence
<220> FEATURE:
<223> OTHER INFORMATION: Amorce primer

<400> SEQUENCE: 4
aaaatctcta gcagtggcgc c                                          21

<210> SEQ ID NO 5
<211> LENGTH: 21
<212> TYPE: DNA
<213> ORGANISM: Artificial Sequence
<220> FEATURE:
<223> OTHER INFORMATION: Amorce primer

<400> SEQUENCE: 5
ggcgccactg ctagagattt t                                          21
```

TOOLS AND METHOD FOR THE DETECTION AND QUANTIFICATION OF GENETICALLY DIVERSE HIV-1, SIVCPZ AND SIV GOR VIRUSES

The invention relates to the detection and quantification of genetically diverse HIV-1, SIVcpz and SIVgor viruses.

It particularly relates to tools and a method for real-time RT-PCR assay (reverse transcription polymerase chain reaction) of high sensitivity to detect and quantify all circulating strains.

In 2009, about 5.2 million people in low- and middle-income countries were receiving antiretroviral therapy (ART) (UNAIDS, 2010) (1). Programs to scale-up ART in resource-limited countries have increased the number of people receiving treatment (i.e. +30% between 2008 and 2009). Nevertheless, viral load (VL) monitoring for patients on ART or for early viral detection in children is only rarely available in resource-limited settings.

Scale-up of laboratory monitoring such as VL measurement in low-income countries is a priority and has been defined as a recommendation by UNAIDS in 2010 to improve the efficiency and quality of HIV antiretroviral treatment and care. Actually, the need of an effective viral load monitoring is justified by different observations.

First, if virological failure is detected early, the spread of drug resistant strains in the general population will decrease.

Second, if a better health intervention and follow-up to patients is provided, their adherence will be increased and possible unnecessary switches to more expensive second line regimens will decrease.

Third, false negative results for 'unusual' strains can lead to inaccurate diagnosis and have adverse consequences.

Lastly, viral load measurement is the best way for early diagnosis of perinatal infection in children (1) (UNAIDS, 2010).

Today, different viral load assays are available and use different techniques of molecular biology such as real-time RT-PCR, NASBA (Nucleic acid sequence based amplification), or bDNA (branched-chain DNA signal amplification) (reviewed in (2)).

If HIV quantification assays are rarely present or only in reference laboratories of resource-limited countries, it is mainly due to their high cost between 50 and 100 dollars (the cost of monitoring is higher than the cost of ART) and their need for specific instruments. Cheaper alternatives to classical molecular based methods have been proposed, but still need further improvement and/or evaluation.

The high genetic diversity of HIV-1 is a major challenge for the development of new, efficient, and sensitive assays.

All commercial quantitative tests were primarily designed on subtype B viruses and, even if they are now more and more adapted to a broad range of variants (some for example include HIV-1 group O), they still do not quantify correctly all circulating variants.

This drawback is particularly an issue for sub-Saharan Africa where non-B strains predominate, and where many and highly diverse HIV-1 variants co-circulate.

Due to globalization, this heterogeneity can also be found in different geographic regions in which the common viral load assays may not be able to detect these 'unusual' strains.

Furthermore, highly divergent viruses, such as HIV-1 groups O, N, and P which also circulate and have a clinical course similar to HIV-1 group M, need appropriate monitoring tools that are not often available.

Thus, HIV diversity and molecular epidemiology still impacts on the management and monitoring of HIV infected patients.

The main limit of the majority of the developed 'in-house' or generic tests is that they were not designed to detect all circulating strains.

For example, the Biocentric Generic HIV-1 Viral Load assay and the "in-house" assay developed by Drosten et al effectively quantily HIV-1 group M but not HIV-1 group O and HIV-1 O and N, respectively (4, 5), because their primers and probe do not correctly match with these divergent strains. On the other hand, a real-time PCR assay developed by Gueudin et al specifically quantifies HIV-1 group O, but does not detect HIV-1 group M strains (6).

This observation is also true for new zoonotic SIV/HIV viruses emerging from SIVs naturally infecting chimpanzees and gorillas (such as HIV-1 group P identified in 2009 emerging from SIVgor (3)).

Besides, recent studies have shown that SIVcpz, ancestors of HIV-1, can be pathogenic for their natural host and previous studies of the inventors have shown how difficult it can be to follow such viral infection in plasma and fecal samples.

To monitor SW infection in naturally infected apes, a new tool should be available to detect SW RNA in fecal samples and to quantify SIV viral load in plasma over the course of infection.

Furthermore, there is still a risk for SIV emergence from infected apes to humans. It will then be important to be able to detect with this same test any hypothetic new emerging SIVcpz or SIVgor viruses in the human population.

Finally, a detection and quantification test would be useful to monitor SIV infection in great apes from both fecal and plasma samples, to understand better the course of SIVcpz and SIVgor infections in their natural hosts, reservoir of the ancestors of HIV-1.

The inventors have searched for new means to overcome the above drawbacks and focused on the design of new tools and a new RT-qPCR assay, relatively inexpensive and at least equal to generic or 'in-house' tests regarding technical characteristics and performance, but with the capacity to virtually detect and quantify all HW-1 circulating strains and their precursors SIVcpz/SIVgor.

The object of the invention is then to provide tools and a method for detecting and quantifying genetically diverse HIV-1, SIVcpz and SIVgor viruses in a test sample with a high sensitivity.

According to another object, the invention provides a single quantitative viral load assay based on the real time RT-PCT technology, satisfying the above mentioned different goals.

The invention thus relates to an oligonucleotide of sequence

SEQ ID No.1: 5'-CTAGAGATCCCTCAGA-3', and the complementary sequence thereof, of sequence SEQ ID No.2:

5'-TCTGAGGGATCTCTAG-3' useful as probes to detect and quantify all HIV-1 circulating forms and their precursors SIVcpz/SIVgor.

Preferably, said probe is a Taqman probe carrying a 5' reporter dye and a 3'minor groove binding-non fluorescent quencher. The reporter dye is for example a fluorochrome dye such as FAM (6-carboxy fluorescein). The quencher is for example MGB (dihydrocyclopyrroindole tripeptide minor groove binder).

Particularly, the invention relates to a primers/probe set wherein the probe is as above defined and the primers comprise two oligonucleotides able to amplify a HIV-1 circulating forms and their precursors SIVcpz/SIVgor target sequence in a test sample.

More particularly the forward primer has sequence

SEQ ID No.3: 5'-SSCTCAATAAAGCTTGCC-3' wherein S represents G or C, and the reverse primer has sequence

SEQ ID No.4: 5+-AAAATCTCTAGCAGTGGCGCC-3' or the complementary sequence thereof of sequence SEQ ID No.5:

3'-GGCGCCACTGCTAGAGATTTT-5'

The target sequence to be amplified by said primers is contained in a test sample which is anything suspected of containing a target sequence such as above defined.

It can be or can be derived from any biological source, such as example blood, biological fluids, plasma, faeces, and tissues. The test sample can be used directly or after a pre-treatment.

The specific design of the probe, particularly of the set of primers and probe enables to practically detect all variants of the HIV-1/SIVcpz/SIVgor lineage with a very high specificity of practically 100%.

The invention also relates to a method for detecting and quantifying in a test sample HIV-1 circulating forms and their precursors SIVcpz/SIVgor, said method comprising the steps of

- forming a reaction mixture comprising a primers/probe set such as above defined and a test sample containing a HIV-1, or precursors thereof SIVcpz/SIVgor target sequence,
- placing the reaction mixture under amplification conditions to form an amplification product and
- detecting the product/probe hybrid as an indication of the presence of said viruses in sample.

The reaction mixture advantageously comprises reagents which are well known for use in nucleic acid amplification reactions.

Such a real-time RT-PCR assay is relatively inexpensive and able to detect and quantify strains from the HIV-1/SIVcpz/SIVgor lineage, including a wide diversity of group M strains and HIV-1 O.

As illustrated by the Examples, the mean PCR efficiency on HIV-1 M plasma, CRF and URF tested was 99%.

Such an assay can therefore be useful in geographical areas of high HIV diversity and at risk for emergence of new HIV variants. Viral load monitoring for patients receiving anti-retroviral therapy or early viral detection in children can be performed by using the invention.

The invention also relates to kits wherein the above defined primers/probe set is packaged in suitable containers and provided with additional reagents, such as amplification reagents.

Other characteristics and advantages of the invention are given in the following Examples. In said Examples it is referred to FIGS. 1-3 which illustrate, respectively FIG. 1, the relationships in pol and env small regions between HIV-1 group O strains tested of Table 1 and HIV-1 group O reference alignment:

the left panel is a phylogenetic tree from a pol region (reverse transcriptase; 689 bp) and the tree on the right is derived from a small env region (gp41; 394 bp). Arrows highlight strains from the panel used in the invention; some strains were not sequenced because of material limitations (small plasma volumes available, low plasma viral load). Other group O sequences used as references are from the HIV database (http://www.hiv.lanl.gov/);

FIG. 2, the phylogenetic relationships between SIVcpz and SIVgor viruses tested to evaluate the RT-qPCR assay of the invention: the tree is derived from a small env region (gp41; 248 bp), constructed by BioNJ (64). White arrows highlight strains from the fecal sample panel used (except from CR4112 amplified in pol region only and CR6278, 6466, 6495, 6534, 6682 amplified in a small 195 by region of gp41) and black (idem) highlight strains from plasma samples. These sequences and others used as references are from the HIV database (http://www.hiv.lanl.gov/); and FIGS. 3A and 3B, the HIV-1 group M RNA viral load quantified by the Generic HIV-1 viral load Biocentric kit and the RT-qPCR assay according to the invention:

A—in total, 185 samples detected with both techniques were plotted on this linearity plot. The solid line represents the fitted regression. Pearson correlation r, 0.95 ($p<0.0001$). The 2.50 log10 copies/ml limit of detection is represented by grey dashed lines.

B—the 185 samples detected with both techniques were plotted on this Bland-Altman difference plot. In vertical axis, the difference between Biocentric and new RT-qPCR assay viral load, against the mean viral load between the two techniques, in horizontal axis. The mean bias on the difference (solid line, $\partial=0.023$ $\log_{10}$ copies/ml) and limits of agreement (dashed lines) are shown on the graphic. On the right vertical axis are represented two main limits: the +/−0.5 $\log_{10}$ copies/ml limit and the CI95 interval (−0.027 to 0.072 $\log_{10}$ copies/ml).

MATERIALS AND METHODS

HIV Negative Plasma Samples

For negative control and specificity determination, 72 HIV negative plasma samples from patients attending a hospital in Yaoundé, Cameroon, for a HIV test were available. The negativity of these samples was determined by diverse HIV serological tests (ICE HIV-1.0.2 (Murex Biotech Limited, Dartford, UK), Wellcozyme HIV Recombinant (Murex), Determine HIV-1/2 (Abbott Laboratories, Tokyo, Japan)).

HIV-1 Group M Plasma Samples

A total of 190 HIV-1 group M RNA extracts from plasma samples were available for viral quantification. Said samples are identified in Table 1 hereinafter.

TABLE 1

| Subtype/CRF | Burundi | Cameroon | DRC | Togo | France | Total |
|---|---|---|---|---|---|---|
| A | 2 | — | 6 | — | — | 8 |
| B | — | — | — | — | 14 | 14 |
| C | 16 | 1 | 3 | — | — | 20 |
| D' | — | 3 | — | — | — | 3 |
| F2 | — | 3 | — | — | — | 3 |
| G | — | — | 2 | 3 | — | 5 |
| H | — | — | 3 | — | — | 3 |
| J | — | — | 3 | — | — | 3 |
| U | — | — | 1 | — | — | 1 |
| CRF01 | — | 2 | 1 | — | — | 3 |
| CRF02 | — | 34 | 3 | 25 | — | 62 |
| CRF06 | — | 2 | — | 3 | — | 5 |
| CRF11 | — | 3 | 1 | — | — | 4 |
| CRF13 | — | — | 1 | — | — | 1 |
| CRF14 | — | 1 | — | — | — | 1 |
| CRF18 | — | 1 | — | — | — | 1 |
| CRF22 | — | 8 | — | — | — | 8 |
| CRF37 | — | — | 1 | — | — | 1 |
| URF | — | 3 | 12 | 6 | — | 21 |
| Unknown/Not done | — | 4 | 2 | 17 | — | 23 |
| Total | 18 | 65 | 39 | 54 | 14 | 190 |

The 190 samples were detected (possibly below the quantification threshold) by Generic HIV-1 viral load Biocentric kit and tested with the method of the invention.

Samples were from four different countries in Africa and from France. The subtypes or CRFs of these HIV-1 group M were determined by pol region genotyping analyses.

Twenty-three samples remained unknown since pol region was not amplified for phylogenetic analyses because VL were below 1000 copies/ml (detection limit of the inhouse drug resistance assay with a 200 UL volume of plasma as input).

All of the samples were previously analytically detected with the Generic HIV-1 viral load Biocentric kit (4) for clinical studies and conserved at −80° C. Their VL ranged between 1.68 and 7.78 $\log_{10}$ copies/ml, with 12 out the 190 plasma samples being analytically detected (PCR amplification) but under the threshold of quantification determined by Biocentric (Biocentric quantification threshold, 2.5 $\log_{10}$ copies/ml) (5). The remaining 178 plasma samples were clinically positives as quantified by the Biocentric technique (above 2.5 $\log_{10}$ copies/ml).

For 167/190 HIV-1 group M positive plasma samples that had a VL superior to 3 $\log_{10}$ copies/ml, a region of approximately 1,865 by in pol (protease and reverse transcriptase regions) was amplified and sequenced as previously described, primarily to determine the drug resistance profile and genotypes for previous studies.

The different subtypes and CRFs are shown in Table 1. The evaluation included plasma samples from four different countries of Africa with different HIV-1 subtypes/CRFs distribution: 18 from Burundi and 54 from Togo with a relatively low genotypic heterogeneity (mainly subtype C and CRF02, respectively), 65 from Cameroon and 39 from DRC with highly diverse subtypes and CRFs. 14 plasma samples with HIV-1 subtype B strains from the hospital of Montpellier, France (34) were also included.

The panel covered the heterogeneity of subtypes and CRFs of HIV-1 group M circulating strains: all subtypes, with the exception of subtype K, were represented, major CRFs were also present, and 21 URFs were included This panel also comprised 23 samples (qualified as "Unknown/ Not done" in table 1 from which genotyping was not possible or not performed due to their low viral loads (<3 $\log_{10}$ copies/ml).

HIV-1 Group O Plasma Samples

The detection and quantification results obtained by RT-qPCR are given in Table 2 below.

TABLE 2

| Sample ID | VL (Real Time Abbott) | VL (new qRT-PCR) | ∂ |
|---|---|---|---|
| Plasma samples for quantification | | | |
| YD1396 | 2.28 | 2.43 | −0.15 |
| C1/378/LIMA | 2.47 | 2.11 | 0.37 |
| YD1431 | 2.53 | 4.22 | −1.69 |
| CM2080 | 3.04 | 3.38 | −0.35 |
| 03/096/A66 | 3.12 | 3.84 | −0.72 |
| YD656 | 3.14 | 4.32 | −1.19 |
| CI973 | 3.18 | 3.21 | −0.03 |
| CM 1070 | 3.29 | 3.51 | −0.22 |
| C1/251/NKPI | 3.65 | 3.70 | −0.06 |
| 2778/07 | 3.68 | 3.61 | 0.07 |
| MR140 | — | 3.64 | New+/Abbott− |
| HJ2464 | — | 3.16 | New+/Abbott− |
| HJ2653 | — | 2.18 | New+/Abbott− |
| HJ2656 | — | 3.25 | New+/Abbott− |

TABLE 2-continued

| Sample ID | VL (Real Time Abbott) | VL (new qRT-PCR) | ∂ |
|---|---|---|---|
| YD593 | — | — | |
| YD594 | — | — | |
| YD603 | — | — | |
| 1689/09 | — | — | |
| 2634/08 | — | — | |
| CI706 | — | — | |
| up0041 | — | — | |
| HJ2722 | — | — | |
| DNA samples for detection | | | |
| HJ020 | | 3.64 | |
| HJ036 | | 4.46 | |
| HJ100 | | 4.00 | |
| HJ162 | | 3.92 | |
| HJ736 | | — | |
| MI159 | | 4.72 | |
| PA206 | | 3.60 | |
| SKPI4077 | | 3.32 | |
| SKPI1015 | | 5.22 | |

Table 2 is divided in two main parts: the upper part for plasma samples, to test HIV-1 group O detection and quantification; the lower part for DNA samples, to test for HIV-1 group O detection. Sample identifications are given. For each sample, the viral loads (VL in $\log_{10}$ copies/ml) obtained from both techniques are given if it could be detected (the negative signs in VL columns reflect undetection of samples) and the difference between them is calculated (∂=VL(Abbott)−VL(new RT-qPCR); in $\log_{10}$ copies/ml). "invention assay +/Abbott −" shows that only the assay of the invention could detect and quantify the corresponding strains.

For HIV-1 group O positive samples, a small region in env (gp41) of approximately 450 by and/or a region in pol (reverse transcriptase) of approximately 1,800 by were amplified and sequenced when enough material was available (14/31 samples).

The group O strains sequenced and tested in this study covered the HIV-1 group O genetic diversity as depicted on FIG. 1.

SIVcpz Plasma Samples from Chimpanzees

Plasma samples from three previously described SIVcpz infected chimpanzees and one non-infected chimpanzee as a negative control were tested.

Two SIVcpz+ chimpanzees (Gab2 and Ch-Go) are from the *Pan troglodytes troglodytes* subspecies and were infected with SIVcpzPtt-Gab2 and SIVcpzPtt-Cam155, respectively.

Figure 2:
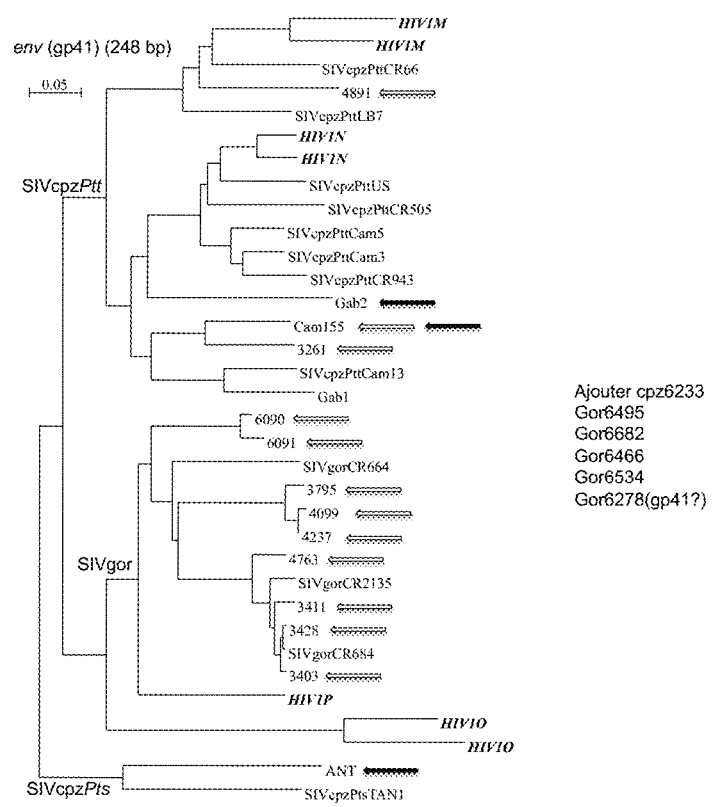

These strains cluster in the SIVcpzPtt/HIV-1M/HIV-1N lineage close to other SIVcpzPtt infecting chimpanzees from Cameroon and Gabon (FIG. 2).

Ch-No, the third SIVcpz positive chimpanzee, is from the *P.t.schweinfurthii* subspecies and was infected with SIVcpz-Pts-ant that clusters in the monophyletic lineage of SIVcpz-Pts strains, out of the SIVcpzPts/SIVgor/HIV-1 lineage (8,9). Sequential plasma samples were available for Ch-Go (two time points seven years apart) and for Ch-No (four time points between October 1989 and January 1991).

The results are given in Table 3 below.

TABLE 3

| Chimpanzee ID | subspecies | SIVcpz | Plasma Sample ID | RNA extraction date | Serology | Detection | Quantification ($\log_{10}$ copies/ml) |
|---|---|---|---|---|---|---|---|
| Ch-Go | *P.t. troglodytes* | SIVcpzPtt-Cam155 | CAM155-01.05.04 | 26.02.09 | + | + | 5.12 |
| | | | CAM155-31.03.11 | 01.04.11[a] | + | + | 4.64* |
| | | | | | | + | 4.92* |
| Gab2 | *P.t. troglodytes* | SIVcpzPtt-Gab2 | GAB2-01.04.88-1 | 12.04.11 | + | + | 3.26 |
| | | | GAB2-01.04.88-2 | 12.04.11 | + | + | 3.29 |

TABLE 3-continued

| Chimpanzee ID subspecies | SIVcpz | Plasma Sample ID | RNA extraction date | Serology | Detection | Quantification ($\log_{10}$ copies/ml) |
|---|---|---|---|---|---|---|
| Ch-No *P.t. schweinfurthii* | SIVcpzPfs-ANT | NOAH-29.09.89 | 12.04.11 | + | − | |
| | | NOAH-27.10.89 | 12.04.11 | + | − | |
| | | NOAH-14.04.90 | 12.04.11 | + | + | 2.68 |
| | | NOAH-08.01.91 | 12.04.11 | + | + | 3.98* |
| Ch-Ni *P.t. schweinfurthii* | Negative | NIKO-07.11.89 | 12.04.11 | − | − | |
| | | NIKO-07.11.89 | 12.04.11 | | | |

HIV/SIV RNA Extraction from Plasma Samples

HIV and SIV RNA were extracted from 200 µl of plasma, conserved at −80° C., using QIAamp Viral RNA Mini kit (Qiagen, Courtabeuf, France) and eluted with 60 µl of elution buffer. Standards and the reproductive control, provided by Generic HIV-1 viral load Biocentric kit (Biocentric, Bandol, France), were culture supernatants of HIV-1 subtype B and were extracted with the same protocol.

Fecal Samples from Wild Living Chimpanzees and Gorillas Infected with SIV 78 fecal samples, conserved in -RNAlater™, from chimpanzees (n=24) and gorillas (n=54) from Cameroon previously described to have HIV-1 cross-reactive antibodies (10, 11).

In these previous studies, fragments in pol and/or gp41 viral regions from five chimpanzee samples (5/24) and from fifteen gorilla samples (15/54) were amplified and sequenced after two to ten independent RNA extractions and subsequent RT-PCR attempts.

These strains represented the genetic diversity of SIVcpz-Ptt and SIVgor viruses Here, total RNA was extracted from 1.5 ml of each ape's fecal sample, using the NucliSens Magnetic Extraction kit (Biomérieux, Craponne, France) as previously described (11), to obtain a final RNA extract volume of 50 µl.

The results obtained are given in Table 4 below.

TABLE 4

| Fecal samples | Individual | RT-PCR amplification after multiple attempts on various RNA extracts[a] | RT-PCR amplification on the given RNA extract[b] | Real-time RT-PCR detection on the given RNA extract[c] | "VL" if detected[d] |
|---|---|---|---|---|---|
| SIVcpzPtt in lee led chimpanzees | | | | | |
| Cam155-1 | Ch-Go | — | — | — | |
| Cam155-4 | | — | — | — | |
| Cam155-2 | | Pos | Pos | Pos | 1.9 |
| Cam155-3 | | Pos | Pos | Pos | 2.56 |
| CR4891 | BYc-ID1 | Pos | — | Pos | 1.63 |
| CR3261 | DJc-ID1 | Pos | — | — | |
| CR6369 | DJc-ID3 | — | — | — | |
| CR5137 | MBc-ID4 | — | — | — | |
| CR5138 | | — | — | — | |
| CR6232 | MBc-ID8 | — | — | — | |
| CR6233 | | Pos | Pos | — | |
| CR6234 | | — | — | — | |
| CR6235 | | — | — | — | |
| CR6236 | | — | — | — | |
| CR6386 | | — | — | — | |
| CR6387 | | — | — | Pos | 2.75* |
| CR6388 | | — | — | Pos | 2.71 |
| CR6254 | MBc-ID9 | — | — | — | |
| CR6405 | MBc-ID11 | — | — | Pos | 2.45* |
| CR6406 | | — | — | — | |
| CR6407 | | — | — | Pos | 2.34 |
| CR6413 | | — | — | — | |
| CR6414 | | — | — | Pos | 2.46 |
| CR6411 | MBc-ID10 | | | | |
| SIVgor infected gorillas | | | | | |
| CR6684 | CPg-ID? | — | — | — | |
| CR3428 | CPg-ID01 | Pos | — | — | |
| CR3428 | | Pos | — | Pos | 1.66 |
| CR6101 | CPg-ID02 | — | — | — | |
| CR6435 | CPg-ID04 | — | — | — | |
| CR6437 | | — | — | — | |
| CR6438 | | — | — | — | |
| CR6451 | | — | — | — | |

TABLE 4-continued

| Fecal samples | Individual | RT-PCR amplification after multiple attempts on various RNA extracts[a] | RT-PCR amplification on the given RNA extract[b] | Real-time RT-PCR detection on the given RNA extract[c] | "VL" if detected[d] |
|---|---|---|---|---|---|
| CR6473 | | — | — | — | |
| CR6477 | | — | — | — | |
| CR6481 | | — | — | Pos | 2.55 |
| CR6485 | | — | — | — | |
| CR6486 | | — | — | — | |
| CR6495 | | Pos | — | — | |
| CR6640 | | — | — | — | |
| CR6641 | | — | — | Pos | 2.57 |
| CR6682 | | Pos | — | — | |
| CR5752 | CPg-ID05 | — | — | — | |
| CR5803 | | — | — | — | |
| CR5804 | | — | — | — | |
| CR5849 | | — | — | — | |
| CR6442 | | — | — | Pos | 1.56 |
| CR6453 | | — | — | — | |
| CR6465 | | — | — | Pos | 2.17 |
| CR6466 | | Pos | — | — | |
| CR6476 | | — | — | — | |
| CR6478 | | — | — | Pos | 2.21 |
| CR6488 | | — | — | — | |
| CR6489 | | — | — | — | |
| CR6685 | | — | — | — | |
| CR2744 | CPg-ID11 | — | — | — | |
| CR2749 | | — | — | — | |
| CR3018 | CPg-ID13 | — | — | — | |
| CR3403 | CPg-ID30 | Pos | — | Pos | 1.65 |
| CR3411 | CPg-ID31 | Pos | — | — | |
| CR6631 | CPg-ID37 | — | — | — | |
| CR6635 | | — | — | — | |
| CR4763 | CPg-ID38 | Pos | Pos | — | |
| CR5832 | CPg-ID60 | — | — | — | |
| CR5816 | CPg-ID65 | | | | |
| CR6484 | | — | — | — | |
| CR6534 | CPg-ID66 | Pos | — | — | |
| CR6555 | | — | — | — | |
| CR5810 | CPg-ID67 | — | — | — | |
| CR6688 | CPg-ID72 | — | — | — | |
| CR6090 | CPg-mixed | Pos | Pos | Pos | 1.66 |
| CR6091 | | Pos | Pos | — | |
| CR3795 | DJg-ID1 | Pos | — | — | |
| CR4099b | DJg-ID2 | Pos | — | Pos | 1.64 |
| CR5265 | DJg-ID3 | — | — | Pos | 1.66 |
| CR4112 | DJg-ID4 | Pos | — | — | |
| CR6259 | DJg-Idx | — | — | Pos | 2.84* |
| CR6278 | | Pos | Pos | Pos | 2.76* |
| CR6279 | | — | — | Pos | 2.59 |
| Total | | 20 | 7 | 21 | |

Development of a Real-time RT-qPCR Assay for Detection and Quantification of Viral Strains from the HIV-1/SIVcpz/SIVgor Lineage The following primers and probe were designed designed using an alignment of sequences from various HIV-1 strains from all four groups (M, N, O, and P), SIVcpzPtt and SIVcpzPts, and SIVgor viruses. The LTR region was firstly explored for its low variability between strains and located the best positions for the primers and the probe.

The forward primer (HXB2 position 523-539) of sequence SEQ ID No. 3: 5'-SSCTCAATAAAGCTTGCC-3') was designed and the reverse primer (HXB2 position 622-642) of sequence SEQ ID No.4: 5'-AAAATCTCTAGCA-GTGGCGCC-3' was as Rouet et al. 2007 (15).

They amplified a small fragment of 120 bp. These primers were set to amplify HIV-1 groups M, N, O, and P, SIVcpzPtt, SIVcpzPts, and SIVgor viruses, since they matched all sequences with 100% homology.

The new probe (HXB2 position 588-603) of sequence SEQ ID No.1: 5'-CTAGAGATCCCTCAGA-3'was a reverse internal TaqMan probe carrying a 5' FAM reporter and a 3' minor groove binding—non-fluorescent quencher (Applied Biosystems, Foster City, Calif.).

The sequence of the probe was designed to bind with all HIV-1 groups (tested sequences) SIVcpzPtt, and SIVgor viruses. Of note one mismatched nucleotide residue at the 3'-end was observed for three SIVcpzPts strains (SIVcpz-PtsTAN1, 2, 3).

All runs were performed in a 20 µl reaction volume containing 10 µl of RNA extract, the primers and the probe at 500 nM, 1× of TaqMan Fast Virus 1-step Master Mix (Applied Biosystems) and RNase-free water to the final volume.

Thermal cycling conditions were as follows: reverse transcription at 50° C. for 5 min, RT inactivation and initial denaturation at 95° C. for 20 sec, and amplification with 50 cycles at 95° C. for 3 sec and 58° C. for 30 sec (total duration ~70 min)

Cycling and data acquisition were carried out using the 7500 Real Time PCR system (Applied Biosystems).

Five standards were used: from the Optiquant™ HIV-1 RNA Quantification Panel (2.78, 3.78, 4.78, 5.78, 6.78 $\log_{10}$ copies/ml) and the Optiquant™ HIV-1 RNA low-positive control (3.78 $\log_{10}$ copies/ml) (Biocentric).

The maximum lower-limit at which a sample can be correctly quantified was assessed by diluting the 3.78 $\log_{10}$ copies/ml standard to two low concentrations (2.50 and 1.78 $\log_{10}$ copies/ml). They were tested in eight replicates.

RT-qPCR Reference Techniques

The Generic HIV-1 viral load Biocentric assay was used as a reference for group M detection and quantification, following the manufacturer's instructions. This Biocentric assay was previously validated as compared to Versant bDNA HIV RNA kit v3.0 (Siemens Healthcare Diagnostics Inc., Deerfield, Ill.) and Amplicor HIV-1 Monitor standard RT-PCR assay v1.5 (Roche Molecular Systems, Pleasanton, Calif.) 5,7) in view of its capacity to detect a wide diversity of HIV-1 group M subtypes and CRFs.

Using 200 µl of plasma, the threshold of the Biocentric assay was set at 2.50 $\log_{10}$ copies/ml. The total duration of the amplification was ~120-140 min.

Cycling and data acquisition were carried out using the ABI Prism 7000 Sequence Detection System or the 7500 Real Time PCR system (Applied Biosystems).

The Abbott m2000rt RealTime™ HIV-1 assay (Abbott Molecular Inc., Des Plaines, Ill.) was used as a reference for group O detection and quantification, since it was previously validated for HIV-1 group O sample quantification. The technique was performed in the IMPM/IRD laboratory in Yaoundé, Cameroon, according to the manufacturer's instructions.

Statistical Analyses

The STATA software package version 10.1 (Stata Corp., College Station, Tex.) was used for all statistical analyses described. The standards and the low-positive control were tested in ten independent runs to determine the reproducibility, the linearity, and the between-run variability of our RT-qPCR technique. Within-run variability was assessed by testing six different samples (five standards and the low-reproductive control) in eight replicates in the same run. The specificity of the assay was calculated as the number of negative samples out of the total number of tested samples from uninfected individuals. The analytical sensitivity for HIV-1 M RNA was calculated as the number of samples detected with the technique according to the invention divided by the number of samples detected with the Biocentric generic assay, including samples under the quantification threshold. Correlation between results from Generic Biocentric test and the RT-qPCR assay of the invention were measured by a Pearson correlation coefficient and by a Spearman rank correlation coefficient for results from each country. A Bland-Altman difference plot for bias and agreement measurements was generated, including limits of agreement (12).

Results

Reproducibility, and Variations between and within Runs.

The inter-assay reproducibility of the standard curve with the RT-qPCR method of the invention was assessed on ten independent assays. In all cases, there was a strong linear correlation between the cycle threshold values found in each experiment and the viral load ($\log_{10}$ copies/ml) with a median correlation coefficient of 1.00 (range, 0.99 to 1.00). The mean slope of the standard curve was −3.33 (range, −3.44 to −3.15), corresponding to a mean amplification efficiency of 99.2%. The standard with the lowest concentration (2.78 $\log_{10}$ copies/ml) was always detected and amplified. The diluted sample at 2.50 $\log_{10}$ copies/ml was always detected and quantified with a low coefficient of variation (inferior to 15%), whereas the diluted sample at 1.78 $\log_{10}$ copies/ml was detected in six out of eight replicates. Thus, our RT-qPCR assay has a quantification threshold inferior to 2.50 $\log_{10}$ copies/ml using an input volume of 200 µl of plasma (limit included in the 1.78-2.50 $\log_{10}$ copies/ml interval). The low-positive control at 3.78 $\log_{10}$ copies/ml was added to each test and was used to further assess the reproducibility and determine the between-run variation. The mean value of this positive control was 3.83 $\log_{10}$ copies/ml (SD, +/−0.19) with a coefficient of variation of 4.8%.

These data are highly similar to what has been determined for the Generic HIV viral load Biocentric assay, confirming a good inter-run reproducibility.

To assess the within-run variation, the standards (n=5) and the low-positive control were each replicated eight times in the same experiment. The low-positive control and the standards were always detected and correctly quantified with a mean coefficient of variation of 4.0% (SD, +/−0.2).

The Analyses of HIV-1 Group M and HIV Negative Samples Show that the Assay has a Good Sensitivity and Specificity.

For the analytical evaluation, a total of 190 HIV-1 group M positive plasma samples were detected by Generic HIV viral load Biocentric assay and tested with the new RT-qPCR test (VL range, 1.68 to 7.78 $\log_{10}$ copies/ml).

Out of them, 185 plasma samples were effectively detected with the technique of the invention (VL range, 2.14 to 8.07 $\log_{10}$ copies/ml).

The analytical sensitivity of the assay according to the invention could be estimated at 97.4% (CI95, 94.0 to 99.1%).

Five samples, with a Biocentric viral load between 2.18 and 3.04 $\log_{10}$ copies/ml, were not detected with our assay, including three under the Biocentric quantification threshold (2.5 $\log_{10}$ copies/ml).

Two samples had a viral load superior to the quantification threshold: one from Cameroon (VL(Biocentric), 3.04 $\log_{10}$ copies/ml) from which no genotype could be obtained despite two amplification attempts in the conserved pol region, and one from DRC (VL, 2.94 $\log_{10}$ copies/ml) with no genotyping available.

The specificity of the test was assessed with 72 HIV negative samples from Cameroon. All samples yielded negative results with our test. Thus, the specificity of the assay was 100% (CI95, 95.9 to 100%).

Excellent correlation between the test according to the invention and the Reference Biocentric Assay for the Quantification of HIV-1 Group M, Irrespective of the Genotype.

Biocentric HIV viral load results and the RT-qPCR assay viral load measures according to the invention were both available for 185 HIV-1 group M plasma samples.

An excellent correlation was found between the results of both assays (Pearson correlation coefficient r=0.95; p<0.0001).

Considering the quantification threshold of 2.5 $\log_{10}$ copies/ml, the Biocentric assay and the RT-qPCR test of the invention quantified 178 and 179 samples above this limit, respectively.

Three samples were under the threshold with both techniques, while four and three samples were under the threshold with Biocentric and the assay of the invention, respectively.

Figure 3:
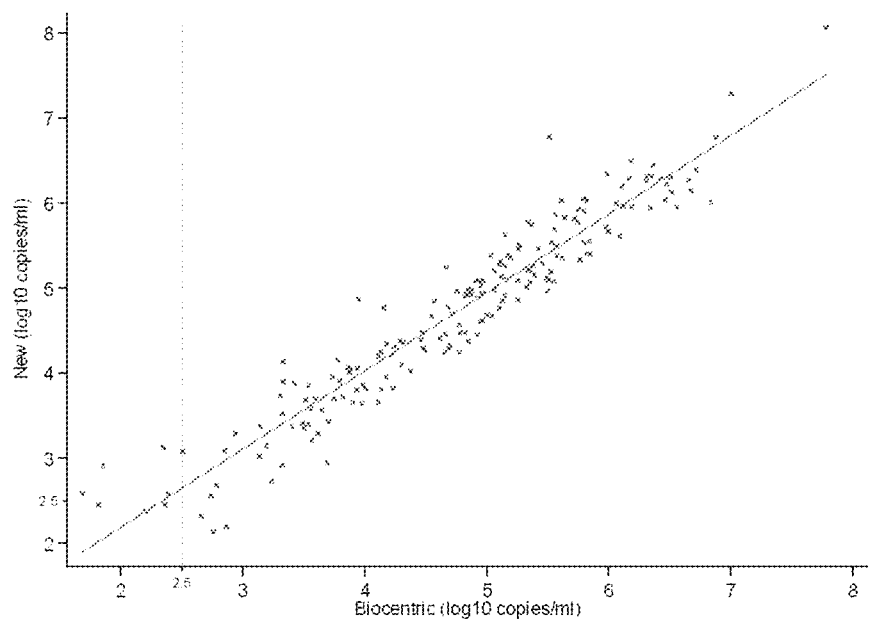
Figure 3:
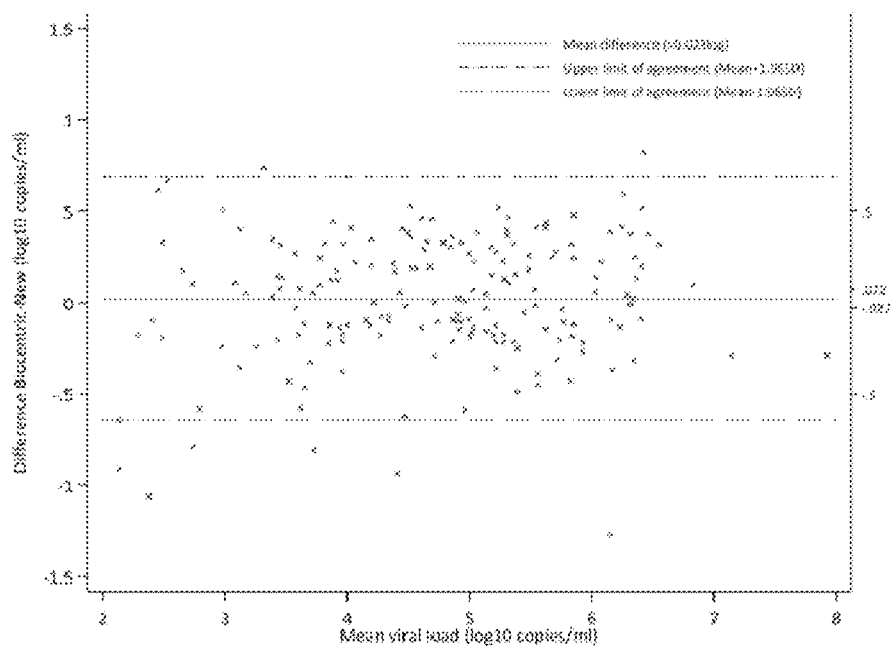

The agreement between the two assays was determined by the Bland-Altman difference plot (FIG. 3B) (12). The mean viral load difference between the two tests was of 0.02 $\log_{10}$ copies/ml and was not significantly different from 0 (p=0.37). Importantly, the difference between both assays did not increase at low or high viral loads (no correlation between the difference and the mean of both assays' viral loads, r=0.09; p=0.24). Standard deviation was of 0.34 $\log_{10}$ copies/ml and the confidence interval 95% was ranging from −0.03 to 0.07, included in the +/−0.50 $\log_{10}$ copies/ml limits (45). In total, 95.1% of the 185 quantified samples were inside the limits of agreement (mean +/−1.96 SD).

Two samples, subtype H and CRF02, had higher viral load with the Biocentric technique (Table 1)

However, seven samples: one subtype B, one CRF22, one CRF37, two CRF02, and two with unknown genotype had higher viral load with our new RT-qPCR method with a mean difference of −0.92 $\log_{10}$ copies/ml.

The tested panel of HIV-1 group M samples was very diverse and covered the genetic diversity of HIV-1 group M subtypes and CRFs. Each subtype or CRF was represented by one to 62 samples. Samples for this study came from four different countries of Africa with very distinct HIV-1 molecular epidemiology and from one hospital in France to determine if these different molecular epidemiological situations would impact negatively on the quantitative assay according to the invention, an assessment of the correlation between Biocentric and the technique of the invention was performed for each studied country.

It was found that for each African country the Spearman correlation coefficient between the two techniques was superior to 0.95 (p<0.0001), irrespective of the molecular epidemiological situation (i.e. the panel from Burundi had samples mostly from subtype C, whereas the panel from DRC harbored a high genetic diversity with 11 different subtypes or CRFs, 12 URFs and 2 from unknown genotype. The test of the invention thus showed very good capacity to quantify the viral load of HIV-1 group M plasma samples, irrespective of the molecular epidemiological situation and the HIV-1 group M genotype.

Detection and Quantification of HIV-1 Group O Strains

31 HIV-1 group O samples were tested for viral detection with the RT-qPCR assay according to the invention, 22 were plasma samples previously tested with Abbott RealTime™ kit and nine were DNA extracts with HIV-1 group O sequence confirmation (Table 2).

With the method of the invention, all ten HIV-1 group O plasma samples that were previously detected with the Abbott kit were detected, showing that the assay of the invention can readily detect HIV-1 group O viruses.

A comparison was then carried out between Viral loads of each plasma sample assessed with the technique of the invention and with Abbott RealTime™ assay.

For seven out of ten HIV-1 group O samples, a good correlation was found with a mean viral load difference of −0.05 $\log_{10}$ copies/ml (range of ∂ VL(Abbott)−VL(new qRT-PCR), −0.35 to 0.37 $\log_{10}$ copies/ml).

Three samples were quantified with a significantly higher viral load than Abbott technique (∂, −0.72, −1.19, and −1.69 $\log_{10}$ copies/ml).

Importantly, four additional HIV-1 group O strains that were undetected by the reference method could be detected. The viral loads of these four samples ranged from 2.18 to 3.64 $\log_{10}$/ml.

Thus, the technique of the invention allowed to detect and quantify more HIV-1 group O viral RNA than the reference method (higher analytical sensitivity, 64% vs 45%) and some samples detected by both methods had higher viral loads with the method of the invention.

As shown by the phylogenetic trees in pol and env regions (FIG. 1) the strains from the panel covered the HIV-1 group O diversity in these regions.

These data clearly show that the technique of the invention provides a better quantification of HIV-1 group O viruses than gold-standard commercial test, irrespective of the genetic diversity.

SIVcpzPtt and SIVcpzPts RNA Detection and Quantification

The SIVcpz strains from the three infected chimpanzees were readily detected with the assay of the invention, while the two plasma samples from Ch-Ni, the SIV negative chimpanzee, were negative (Table 3), showing that the RT-qPCR assay of the invention was able to specifically detect both SIVcpzPts and SIVcpzPtt strains.

Plasma samples from Cam155 were all detected and quantified and had viral loads of approximately 5 $\log_{10}$ copies/ml (Table 3).

Previously, the quantification of the plasmatic SIVcpzPttCam155 RNA concentration was also carried out with the bDNA assay in 2004 (Versant HIV-1 RNA 3.0) and the Abbott RealTime™ test in 2011. In 2004, the VL(Versant) was 5.09 $\log_{10}$ copies/ml, not significantly different from the viral load found with the RT-qPCR assay of the invention. However, a viral load of 3.76 $\log_{10}$ copies/ml was found with the Abbott test in 2011, which was significantly lower than with the technique of the invention (∂, −1.02 $\log_{10}$ copies/ml).

The assay of the invention allowed to detect and quantify SIVcpzPttGab2 from a plasma sample of chimpanzee Gab2 drawn in April 1988. Two independent RNA extractions and quantifications were performed and similar viral loads around 3 $\log_{10}$ copies/ml (Table 3) were found. The strain infecting Ch-No is from the SIVcpzPts lineage, a clade more divergent from HIV-1 than SIVcpzPtt. However, the test of the invention was still able to detect and quantify this divergent variant. For Ch-No, four sequential blood samples taken between September 1989 and January 1991 were used: the first two at the end of 1989 had an undetectable viral load and the last two in April 1990 and January 1991 had detectable viral loads of 2.68 and 3.98 $\log_{10}$ copies/ml, respectively.

Previously, Kestens and colleagues observed a fluctuating pattern with the measurement of viral titers in plasma varying from undetected to 1,000 TCID/ml. From the end of 1997 to 2001 (i.e. dates after the panel of the invention), Ondoa et al. quantified viral RNA from Ch-No plasma samples with a specific in-house assay and values varied from 3.93 to 5.80 $\log_{10}$ copies/ml (13,14) in the range of the viral loads found according to the invention.

Therefore, despite the high genetic distances between SIVcpz strains, the assay according to the invention was able to detect and quantify the SIVcpzPtt and SIVcpzPts RNA from chimpanzee plasma samples.

SIVcpz and SIVgor Detection from Fecal Samples

Here, the detection of SIVcpzPtt and SIVgor viral RNA from fecal samples was tested (i) to determine if the real-time RT-PCR assay of the invention was able to detect both types of viruses, direct ancestors of all HIV-1 groups, and (ii) to test whether this assay was enough sensitive for viral detection in fecal samples.

24 fecal samples from nine different P.t.troglodytes chimpanzees were tested by serology, to be infected with SIVcpz-Ptt. Since these chimpanzees were from four different locations in south Cameroon and because of the phylogeographic clustering of SIVcpzPtt, the viruses tested were expected to have high genetic distances between them, which could be confirmed for four of them.

Here, from a unique RNA extract, SIVcpzPtt could be amplified from only three fecal samples (corresponding to two individuals) with the conventional RT-PCR, while SIVcpzPtt could be detected from eight fecal samples (corresponding to four individuals) with the real-time RT-PCR assay (Table 4).

Sequence analyses confirmed that the amplified LTR fragments were corresponding to SIVcpzPtt. It is thus possible to detect SIVcpzPtt in fecal samples using this real-time RT-PCR system. The sensitivity of the assay according to the invention is better than with conventional RT-PCR.

In addition, 54 fecal samples from 22 G.g.gorilla individuals from Cameroon previously shown, by serology, to be infected with SIVgor were tested.

In previous studies of the inventors, SIVgor small fragments were amplified and sequenced with a conventional RT-PCR in only 15 samples after multiple extractions and amplification attempts.

Here, on a unique RNA extract, SIVgor viruses from only four fecal samples (corresponding to three infected gorillas) could be amplified with the conventional RT-PCR, while SIVgor viruses could be detected in 13 fecal samples (corresponding to eight individuals) with the real-time RT-PCR assay of the invention (Table 4).

By LTR sequencing analyses, it was confirmed that the amplified fragments were corresponding to SIVgor.

The above results clearly establish that the method of the invention is thus able to detect SIVgor viruses in fecal samples.

After one attempt, the real-time assay of the invention was able to detect SIVgor strains on 24% of the samples, compared to only 7% with the conventional method.

As shown by the above results, the tools and real-time RT-PCR assay of the invention allow to detect and quantify a wide range of HIV-1 variants and their progenitors SIVcpz and SIVgor, infecting chimpanzees and gorillas respectively. The cost per reaction was comparable to costs of other generic or 'in-house' assays and most importantly, highly inferior to commercial tests around 50-100 $ per reaction.

Advantageously, the assay of the invention has a high PCR efficiency with low variations between and within runs (coefficients of variation, 4.8% and 4.0%, respectively). The quantification threshold was inferior to 2.50 $\log_{10}$ copies/ml (range, 1.68 to 2.50) with an input volume of 200 μl, which is comparable with commercial assays with the same input volume. These technical characteristics are also similar to those reported for other generic or 'in-house' assays.

The specificity of the test according to the invention was 100% (CI95, 95.9-100%). This parameter is essential for a good viral load assay since a false positive result could have adverse consequences for a patient on ART with a normally undetectable viral load. The analytical sensitivity of this new real-time assay, 97.4% (CI95, 94.0 to 99.1%), was calculated on 190 HIV-1 group M positive samples previously tested with the Generic Biocentric kit (VL range, 1.68 to 7.78 $\log_{10}$ copies/ml). Eight samples with a viral load between 2.5 and 3 $\log_{10}$ copies/ml were effectively detected and seven others with a viral load inferior to 2.5 $\log_{10}$ copies/ml according to the Biocentric assay could be detected by using the test of the invention.

The Generic Biocentric assay and the RT-qPCR test according to the invention are highly correlated (r=0.95, p<0.0001) with no significant difference between their mean viral load (p=0.37) as tested on 185 HIV-1 group M samples (range, 1.68 to 7.78 $\log_{10}$ copies/ml), and 95.1% of quantified samples were within the limits of agreement between the two methods (mean +/−1.96 SD) (12). Seven samples from various subtypes were significantly better quantified with the method of the invention ($\partial$>+/−0.5 $\log_{10}$ copies/ml). Importantly, three of them had viral loads under the Biocentric threshold but were quantified with the assay of the invention above the 2.5 $\log_{10}$ copies/ml limit.

The panel used according to the invention included HIV-1 group M samples from five different countries (four in Africa and one in Europe) with very diverse HIV-1 subtype/CRF distribution, including 39 samples from DRC and 65 from Cameroun, two countries with an extensive genetic diversity. For each country, an excellent correlation was found between both VL methods' results, showing that HIV-1 group M diversity did not impact negatively on the viral quantification performed according to the invention. This aspect is of major importance, and VL assays should always be validated and further evaluated in different countries with different molecular epidemiological features, as it has been done for previous 'in-house' assays developed for resource-limited settings.

Unlike previously described 'in-house' tests, the RT-qPCR assay of the invention was also able to detect and quantify HIV-1 group O viruses from plasma samples. Importantly, out of 22 group O samples, four samples that were not detected by the Abbott Real-time™ assay were detected and quantified by carrying out the assay of the invention and higher viral loads were measured in three samples ($\partial$, −1.69 to −0.72), showing that the method of the invention is more sensitive than the commercial assay.

In the experiments carried out according to the invention, a significantly high number of HIV-1 group O strains (22 plasma samples and nine DNA extracts representing 31 different HIV-1 O strains) was tested Importantly, the group O panel covered HIV-1 group O genetic diversity, reflecting that the high genetic diversity of this group did not impact on the detection. The new assay has then the capacity to detect highly divergent strains (HIV-1 groups N and P) as found in only few cases in humans, since it can detect genetically distant SIVcpz and SIVgor strains.

Because of the ongoing risk of cross-species transmissions of SIVs from apes to humans and the necessity to follow SIVcpz and SIVgor infection in their natural hosts to better understand the pathogenicity of these HIV-1 progenitors in their natural hosts, the assay was also develop with the goal to detect and quantify all viruses from the HIV-1/SIVcpz/SIVgor Glade.

As shown by the results given above, the assay of the invention is particularly useful to detect and quantify SIVcpzPtt and SIVcpzPts viruses in plasma samples from western and eastern central African chimpanzees. Plasmatic SIVcpz viral loads found in naturally infected chimpanzees appear to be in the range of HIV-1 viral loads in humans. Besides, SIVcpzPtt was detected from 33% of SW seropositive chimpanzee fecal samples with the real-time assay of the invention, versus an amplification success (at first attempt) of 13% on the same panel with a basic RT-PCR in pol or env small fragments. The test was also able to detect SIVgor viruses, precursors of HIV-1 group P and probable ancestors of HIV-1 group O.

SIVgor strains were amplified from 24% of 54 SW seropositive gorilla fecal samples versus 7% of amplification success on the same panel at first attempt with a conventional RT-PCR using SIVgor specific primers targeting a gp41 small fragment.

The new assay can be a good complement to basic RT-PCR to confirm viral presence in seropositive samples. The results also confirm that SIVcpz and SIVgor viral loads are very low in fecal samples. Interestingly, SIVcpzPtt viral loads from both plasma and fecal samples could be tested for Ch-Go, and a more than 100-fold difference between both compartments (Tables 3 and 4, first lines) was found. The amplification of such divergent variants, SIVcpz and SIVgor, was not possible with the Biocentric technique, and SIVcpz quantification seemed suboptimal with Abbott Real-Time™ assay. Therefore, the real-time RT-PCR test of the invention is a new opportunity to detect possible new emerging simian immunodeficiency viruses from apes to humans.

In conclusion, the invention provides a relatively low-cost real-time RT-PCR assay able to detect and quantify all viral strains from the HIV-1/SIVcpz/SIVgor Glade, meaning that HIV-1 diversity is covered and that HIV-1 precursors can also be monitored. This new test is thus a breakthrough in the field of viral load quantification since it could monitor any HIV-1 strains currently circulating in humans but could also detect new SIV emergences of SIVcpz/SIVgor in humans.

REFERENCES

1. Lambert, J. S., D. R. Harris, E. R. Stiehm, J. Moye, Jr., M. G. Fowler, W. A. Meyer, 3rd, J. Bethel, and L. M. Mofenson. 2003. Performance characteristics of HIV-1 culture and HIV-1 DNA and RNA amplification assays for early diagnosis of perinatal HIV-1 infection. J Acquir Immune Defic Syndr 34:512-519.

2. Fiscus, S. A., B. Cheng, S. M. Crowe, L. Demeter, C. Jennings, V. Miller, R. Respess, and W. Stevens. 2006. HIV-1 viral load assays for resource-limited settings. PLoS medicine 3:e417.

3. Plantier, J. C., M. Leoz, J. E. Dickerson, F. De Oliveira, F. Cordonnier, V. Lemee, F. Damond, D. L. Robertson, and F. Simon. 2009. A new human immunodeficiency virus derived from gorillas. Nature medicine 15:871-872.

4. Drosten, C., M. Panning, J. F. Drexler, F. Hansel, C. Pedroso, J. Yeats, L. K. de Souza Luna, M. Samuel, B. Liedigk, U. Lippert, M. Sturmer, H. W. Doerr, C. Brites, and W. Preiser. 2006. Ultrasensitive monitoring of HIV-1 viral load by a low-cost real-time reverse transcription-PCR assay with internal control for the 5' long terminal repeat domain. Clinical chemistry 52:1258-1266.

5. Rouet, F., D. K. Ekouevi, M. L. Chaix, M. Burgard, A. Inwoley, T. D. Tony, C. Danel, X. Anglaret, V. Leroy, P. Msellati, F. Dabis, and C. Rouzioux. 2005. Transfer and evaluation of an automated, low-cost real-time reverse transcription-PCR test for diagnosis and monitoring of human immunodeficiency virus type 1 infection in a West African resource-limited setting. J Clin Microbiol 43:2709-2717.

6. Gueudin, M., J. C. Plantier, F. Damond, P. Rogues, P. Mauclere, and F. Simon. 2003. Plasma viral RNA assay in HIV-1 group O infection by real-time PCR. Journal of virological methods 113:43-49.

7. Rouet, F., M. L. Chaix, E. Nerrienet, N. Ngo-Giang-Huong, J. C. Plantier, M. Burgard, M. Peeters, F. Damond, D. K. Ekouevi, P. Msellati, L. Ferradini, S. Rukobo, V. Marechal, N. Schvachsa, L. Wakrim, C. Rafalimanana, B. Rakotoambinina, J. P. Viard, J. M. Seigneurin, and C. Rouzioux. 2007. Impact of HIV-1 genetic diversity on plasma HIV-1 RNA Quantification: usefulness of the Agence Nationale de Recherches sur le SIDA second-generation long terminal repeat-based real-time reverse transcriptase polymerase chain reaction test. J Acquir Immune Defic Syndr 45:380-388.

8. Peeters, M., K. Fransen, E. Delaporte, M. Van den Haesevelde, G. M. Gershy-Damet, L. Kestens, G. van der Groen, and P. Piot. 1992. Isolation and characterization of a new chimpanzee lentivirus (simian immunodeficiency virus isolate cpz-ant) from a wild-captured chimpanzee. AIDS 6:447-451.

9. Vanden Haesevelde, M. M., M. Peeters, G. Jannes, W. Janssens, G. van der Groen, P. M. Sharp, and E. Saman 1996. Sequence analysis of a highly divergent HIV-1-related lentivirus isolated from a wild captured chimpanzee. Virology 221:346-350.

10. Neel, C., L. Etienne, Y. Li, J. Takehisa, R. S. Rudicell, I. N. Bass, J. Moudindo, A. Mebenga, A. Esteban, F. Van Heuverswyn, F. Liegeois, P. J. Kranzusch, P. D. Walsh, C. M. Sanz, D. B. Morgan, J. B. Ndjango, J. C. Plantier, S. Locatelli, M. K. Gonder, F. H. Leendertz, C. Boesch, A. Todd, E. Delaporte, E. Mpoudi-Ngole, B. H. Hahn, and M. Peeters. 2010. Molecular epidemiology of simian immunodeficiency virus infection in wild-living gorillas. Journal of virology 84:1464-1476.

11. Etienne, L., S. Locatelli, A. Ayouba, A. Esteban, C. Butel, F. Liegeois, A. Aghokeng, E. Delaporte, E. Mpoudi Ngole, and M. Peeters. 2012. Non-invasive follow-up of simian immunodeficiency virus infection in wild-living non-habituated western lowland gorillas in Cameroon. Journal of virology.

12. Bland, J. M., and D. G. Altman. 1999. Measuring agreement in method comparison studies. Statistical methods in medical research 8:135-160.

13. Ondoa, P., L. Kestens, D. Davis, C. Vereecken, B. Willems, K. Fransen, J. Vingerhoets, G. Zissis, P. ten Haaft, J. Heeney, and G. van der Groen. 2001. Longitudinal comparison of virus load parameters and CD8 T-cell suppressive capacity in two SIVcpz-infected chimpanzees. Journal of medical primatology 30:243-253.

14. Ondoa, P., D. Davis, B. Willems, L. Heyndrickx, L. Kestens, I. van der Berg, S. Coppens, W. Janssens, J. Heeney, and G. van der Groen. 2001. Genetic variability of the V1 and V2 env domains of SIVcpz-ant and neutralization pattern of plasma viruses in a chimpanzee infected naturally. Journal of medical virology 65:765-776.

15. Rouet, F., H. Menan, J. Viljoen, N. Ngo-Giang-Huong, K. Mandaliya, D. Valea, T. X. Lien, S. Danaviah, D. Rousset, A. Ganon, and E. Nerrienet. 2008. In-house HIV-1 RNA real-time RT-PCR assays: principle, available tests and usefulness in developing countries. Expert review of molecular diagnostics 8:635-650.

The invention claimed is:

1. A method for detecting and quantifying by RT-qPCR HIV-1 and its precursors SIVcpz and SIVgor in a test sample, said method comprising the steps of:

forming a reaction mixture comprising a primers/probe set and a test sample containing HIV-1, or precursors thereof SIVcpz/SIVgor, target sequence, placing the reaction mixture under amplification conditions to form an amplification product, forming a hybrid between the amplification product and a probe of said primers/probe set, and detecting and quantifying the hybrid as an indication of the presence of HIV-1, SIVcpz or SIVgor in the test sample, wherein the primers/probe set consists of:
(i) a forward primer consisting of SEQ ID NO: 3, or the complement thereof;
(ii) a reverse primer consisting of SEQ ID NO: 4, or the complement thereof consisting of SEQ ID NO: 5; and
(iii) the probe consisting of SEQ ID NO: 1, or the complement thereof consisting of SEQ ID NO: 2.

2. A method for detecting and quantifying by RT-qPCR HIV-1 and its precursors SIVcpz and SIVgor in a test sample, said method comprising the steps of:

forming a reaction mixture comprising a primers/probe set and a test sample containing a HIV-1, or precursors thereof SIVcpz/SIVgor target sequence, placing the reaction mixture under amplification conditions to form an amplification product forming a hybrid between the amplification product and a probe of said primers/probe set, and detecting and quantifying the hybrid as an indication of the presence of HIV-1, SIVcpz or SIVgor in the test sample, wherein the primers/probe set consists of:

(i) a forward primer consisting of SEQ ID NO: 3, or the complement thereof;

(ii) a reverse primer consisting of SEQ ID NO: 4, or the complement thereof consisting of SEQ ID NO: 5; and (iii) the probe consisting of SEQ ID NO: 1, or the complement thereof consisting of SEQ ID NO: 2, said probe having a fluorescent marker at the 5' position and a quencher at the 3' position.

* * * * *